(12) United States Patent
Edwards et al.

(10) Patent No.: US 6,440,159 B1
(45) Date of Patent: Aug. 27, 2002

(54) MULTIUSE THERAPY WRAP

(76) Inventors: Joseph H. Edwards, 2210 E. Laird Way, Salt Lake City, UT (US) 84108; Michael J. Carey, 6817 Elaine Way, San Diego, CA (US) 92120

( * ) Notice: Subject to any disclaimer, the term of this patent is extended or adjusted under 35 U.S.C. 154(b) by 0 days.

(21) Appl. No.: 09/516,548

(22) Filed: Mar. 1, 2000

(51) Int. Cl.[7] .................................................. A61F 7/00
(52) U.S. Cl. ........................ 607/108; 607/112; 607/114
(58) Field of Search ................................. 607/108, 109, 607/112, 114; 602/2, 14

(56) References Cited

U.S. PATENT DOCUMENTS

| | | | |
|---|---|---|---|
| 3,074,250 A | * | 1/1963 | Everett .......................... 62/259 |
| 4,805,620 A | * | 2/1989 | Meistrell ...................... 128/402 |
| 4,964,402 A | | 10/1990 | Grim et al. |
| 4,972,832 A | | 11/1990 | Trapini et al. |
| 4,976,262 A | | 12/1990 | Palmacci |
| 5,000,176 A | * | 3/1991 | Daniel .......................... 128/402 |
| 5,020,536 A | * | 6/1991 | Keen ............................ 128/402 |
| 5,020,711 A | * | 6/1991 | Kelley .......................... 224/222 |
| 5,092,318 A | | 3/1992 | More et al. |
| 5,133,348 A | | 7/1992 | Mayn |
| 5,139,477 A | | 8/1992 | Peters |
| 5,146,625 A | | 9/1992 | Steele et al. |
| 5,148,804 A | | 9/1992 | Hill et al. |
| 5,185,000 A | | 2/1993 | Brandt et al. |
| 5,215,080 A | | 6/1993 | Thomas et al. |
| 5,230,335 A | | 7/1993 | Johnson, Jr. et al. |
| 5,274,865 A | | 1/1994 | Takehashi |
| 5,304,216 A | | 4/1994 | Wallace |
| 5,393,462 A | | 2/1995 | Avery |
| 5,400,806 A | | 3/1995 | Taylor |
| 5,407,420 A | | 4/1995 | Bastyr et al. |
| 5,407,421 A | | 4/1995 | Goldsmith |
| 5,431,622 A | | 7/1995 | Pyrozyk et al. |
| 5,466,251 A | | 11/1995 | Brunson et al. |
| 5,476,492 A | | 12/1995 | Unrug |
| 5,496,358 A | | 3/1996 | Rosenwald |
| 5,514,170 A | | 5/1996 | Mauch |
| 5,534,020 A | | 7/1996 | Cheney, III et al. |
| 5,728,147 A | * | 3/1998 | Thomas ....................... 607/112 |
| 5,733,321 A | | 3/1998 | Brink |
| 5,741,220 A | | 4/1998 | Brink |
| 5,785,716 A | * | 7/1998 | Bayron et al. ............... 607/108 |
| 5,800,490 A | | 9/1998 | Patz et al. |
| 5,860,945 A | * | 1/1999 | Cramer et al. ................. 602/62 |
| 6,261,314 B1 | * | 7/2001 | Rich ............................ 607/109 |

OTHER PUBLICATIONS

Dr. Leonard's Healthcare Catalog, 1995, p. 5.
The Sharper Image, Father's Day 2000 Catalog, p. 37.

* cited by examiner

Primary Examiner—Linda C. M. Dvorak
Assistant Examiner—Jocelyn Ram
(74) Attorney, Agent, or Firm—Holme Roberts & Owen

(57) ABSTRACT

A wrap is configured for positioning at different sites including the ankle, calf, knee, thigh, lower arm, elbow, upper arm, neck, shoulder and torso including the lower back. The wrap is formed from laminated closed-cell neoprene so that it is elastically deformable. The wrap has a therapy section with a pocket sized to receive a gel pack that can be heated or cooled to apply the desired thermal therapy. Long connecting ears extend outwardly near the top of the therapy section and short connecting ears extend outwardly near the bottom. One ear of the long connecting ears and one ear of the short connecting ears has the hook portion of a hook and pile type connector with the material laminated to the neoprene selected to function as the pile portion of a hook and pile type connector. A strap also formed from closed-cell neoprene has a material laminated to function as the pile portion and has a hook portion at one end. The strap is attached to the long ears to extend as needed so that the wrap may be positioned about the shoulder, torso and neck of the user.

25 Claims, 9 Drawing Sheets

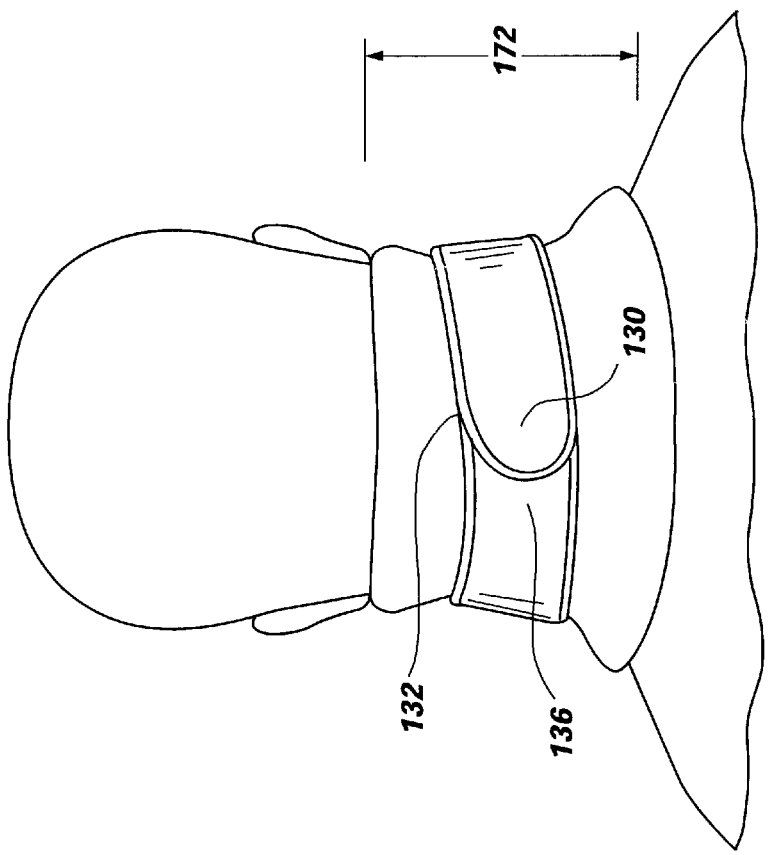
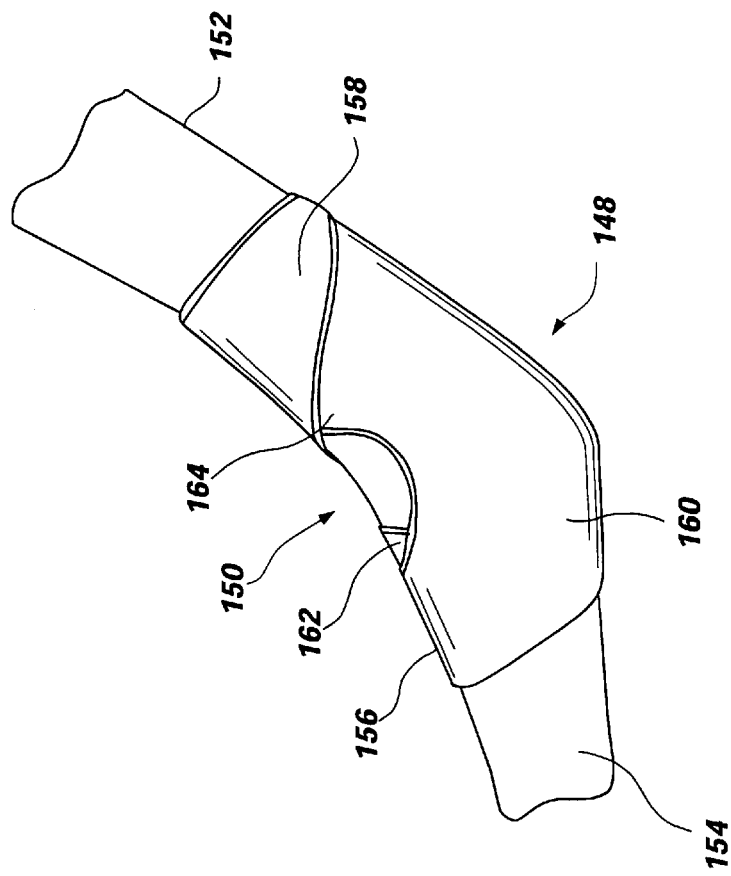
Fig. 7
Fig. 6

MULTIUSE THERAPY WRAP

BACKGROUND OF THE INVENTION

1. Field

This invention relates to devices that are positioned about a portion of the body for the purposes of applying thermal therapy and specifically to a device configured for positioning about any one of several different or multiple sites on or portions of the body and methods of applying the device at each site of the multiple sites on portions of the body and even more specifically to methods for applying thermal therapy with one apparatus adapted for use about each of the ankle, calf, knee, thigh, lower arm, elbow, upper arm, shoulder, neck and torso.

2. State of the Art

A treating health care professional may request the patient apply thermal therapy to a portion of the body as part of a desired medical treatment. Thus, cold may be applied to reduce swelling or heat may be applied to assist in ameliorating the symptoms or conditions of other maladies. Devices for applying thermal therapy to a body portion such as a joint or muscle portion are known. For example, U.S. Pat. No. 4,964,402 (Grim, et al.) discloses a device in which a gel pack is positioned against a body part. The gel pack may be heated or cooled so that the desired therapy is applied as desired.

U.S. Pat. No. 4,972,832 (Trapini) discloses another device for strapping a thermal therapy unit to a body portion. U.S. Pat. No. 4,976,262 (Palmacci) discloses a device for attaching thermal therapy devices to a body portion in which VELCRO® type connectors are used to connect ends of a wrapping or securing structure. U.S. Pat. No. 5,148,804 (Hill, et al.) shows a device with a pocket for a thermal pack.

Therapy wraps are shown with structure for attachment to a joint like a knee and along a body limb such as the leg or arm. U.S. Pat. No. 4,964,402 (Grim, et al.) shows use around the ankle, knee, and wrist. U.S. Pat. No. 4,976,262 (Palmacci) shows several different structures to hold a thermal device like an ice pack to limb joints and also a structure to hold a thermal device to the shoulder using elastic or stretchable material.

The disclosed devices in the art are formed to be used at one location or at locations on a limb but not at locations in addition to the limb such as about one of the neck, the shoulder and the torso including the lower back. A single device in which thermal therapy may be applied to locations on the limbs of a patient as well as to a shoulder, the neck and the torso including the lower back is desired and not known.

SUMMARY OF THE INVENTION

A wrap for applying thermal therapy to a patient has a therapy section with a pocket sized to receive and retain a thermal unit that functions as a reservoir of material at a desired temperature attained chemically or by heating or cooling as desired. The therapy section has a top, a bottom, a left side and a right side and is appropriately sized for positioning at several different sites on the body or about each of several selected body elements of a patient. Long connecting means are attached to the therapy section proximate either the top or the bottom. The long connecting means has a left section extending outwardly from the left side of the therapy section a first length and a right section extending outwardly from the right side of the therapy section a second length.

Long attaching means has a first attaching element attached to or formed with the left section of the long connecting means and a second attaching element attached to or formed with the right section of said long connecting means. The first and second attaching elements are operable for removably securing one to the other and for removably attaching the left section and the right section together to form an opening adjustable in size to receive a selected body element of a patient therein and for attaching said therapy section to and about the body element to cause thermal energy from the thermal unit to be applied to the body element.

Short connecting means is attached to the therapy section proximate the other of the top and the bottom of the therapy section. The short connecting means has a left section extending outwardly from the left side a third length and a right section extending outwardly from the right side a fourth length. The third length and the fourth length are selected so that the total length of the third and fourth lengths together is less than the total of the first length and the second length together. The short attaching means has a first attaching element attached to or formed with the left section of the short connecting means and a second attaching element attached to or formed with the right section of the short connecting means for removably attaching themselves together and in turn the left section and the right section of said short connecting means together to form an opening adjustable in size for positioning about the selected body element of a patient spaced from the long connecting means and for attaching the therapy section to the body element so that thermal therapy may be applied to the body element.

The therapy wrap also preferably includes a strap having a first end and a second end. Strap attaching means is positioned proximate the first end and the second end for removable connection to each other. The strap attaching means includes a first element and a second element for removable connection to each other or to one of the first element and the second element of the long attaching means or to one of the first element and the second element of the short attaching means to extend about a selected body element.

In preferred configurations of the wrap, the long connecting means and the short connecting means, and also desirably the strap, are formed from an elastically deformable material such as a closed-cell neoprene. The closed-cell neoprene is preferably laminated on its opposite surfaces with a polyester material that has a surface that will function as the pile portion of a hook and pile connector arrangement. In turn, the wrap is in effect infinitely adjustable. That is, the first attaching element and the second attaching element of both the long attaching means and the short attaching means as well as strap attaching means are the hook portion and the pile portion of a hook and pile connector arrangement in which the polyester material laminated to the closed-cell neoprene is VELCRO® compatible or a VELCRO® mate so that it functions as the pile portion.

In preferred configurations, the first length and the second length are selected to be equal and the third length and the forth length are also selected to be equal. The first and second length are selected so that the body wrap is sized to extend around the upper thigh and in turn will be of sufficient length to extend around other parts of the several limbs of a patient. The third length and the fourth length are selected to also extend about the thigh but at a point spaced from the first and second lengths and at a point where the circumference of the thigh is smaller. In turn, the third length and the fourth length will be of sufficient length to extend about other parts of the several limbs of a patient.

In specific arrangements, the thermal section of the wrap is rectilinear in shape or projection having a height selected to extend at least about half the length of a thigh or calf and a width to extend around at least about half the circumference of a thigh of a user. The pocket is formed by attaching an elastically deformable material such as LYCRA® to the therapy section. The pocket is sized to receive the thermal unit therein.

Methods of use of the wrap include first heating or cooling the thermal unit to a desired temperature and then positioning it in the pocket formed in the therapy section. The wrap is then positioned or wrapped about a selected portion, part or element of the body with the thermal unit in the pocket. The long connecting means and the short connecting means are positioned about the selected portion, part or element of the body. The respective first elements are positioned proximate the respective second elements of the long attaching means and the short attaching means and are thereafter urged together to effect a removable connection.

The strap may be positioned about the wrap when positioned on a limb. That is, the strap may be wound about the wrap snugly or in tension as a further means of attaching the wrap to the limbs of a user such as the ankle, calf, knee, thigh, lower arm, upper arm, elbow and upper thigh. In selected applications, the first end of the strap may be connected to the first element or the second element of the long connecting means or to the short connecting means. When the strap is attached to the long connecting means, the wrap may be positioned about the shoulder with the strap extending about the torso under the arm opposite the shoulder about which the wrap is placed. The short attaching means attach about the upper arm extending from the shoulder about which the wrap is placed.

Preferred methods include the selection of a wrap formed of an elastically deformable material and stretching the wrap about the portion of the body to which the wrap is to be applied.

The long connecting means and the short connecting means are each preferably made of an elastically deformable material and stretched about the body portion or element to tensionally secure the wrap thereto applying, in turn, not only thermal therapy but also compressive therapy.

Methods for positioning the wrap about the torso or trunk of a user include first positioning the left section and the right section of the long attaching means about the torso of a patient with the therapy section positioned against and about the torso at a desired location such as the lower back. The first attaching element and the second attaching element of the long attaching means are joined to one of the first attaching element and the second attaching element of the strap. The other of the first attaching element and the second attaching element of the long attaching means is then urged into connection with the other of the first attaching element or the second attaching element of the strap to snugly secure the therapy section to the torso. A second belt or strap which may be preferably the waist band or belt of a garment (e.g., the pants or trousers) of a user acts to hold by the short connecting means and the portions of the therapy section thereinbetween in place.

Methods of positioning the wrap about the neck involve folding the therapy section to fit about the neck of a patient, positioning the therapy section about the neck of a patient and wrapping the strap about the therapy section and the neck and attaching the first element of the strap attaching means and the second element of the strap attaching means to each other to secure the wrap in place.

BRIEF DESCRIPTION OF THE DRAWINGS

In the drawings, which illustrate what is presently regarded as the best mode for carrying out the invention:

FIG. 6 is a depiction of the therapy wrap of the present invention positioned about the ankle of a user;

FIG. 7 is a depiction of the therapy wrap of the present invention positioned about the neck of a user;

DESCRIPTION OF THE ILLUSTRATED EMBODIMENTS

Figure 1:
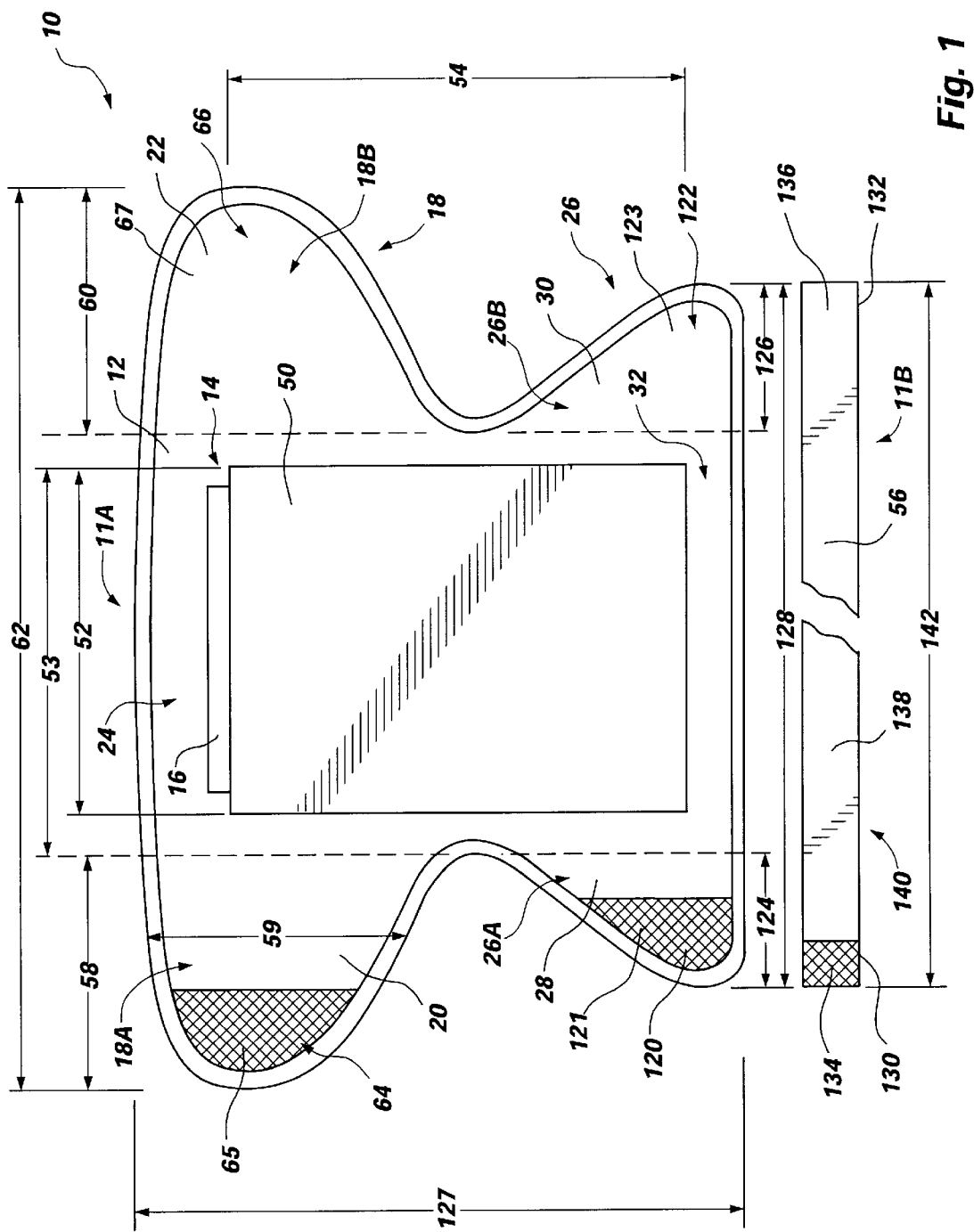
FIG. 1 is a plan view of a therapy wrap of the present invention.

A wrap 10 for applying thermal therapy includes a body wrap 11A configured for placement about the body with a first strap 11B for use with the body wrap 11A to hold it in place in selected applications or at selected body locations. The body wrap 11A has a therapy section 12 having a pocket 14 sized for receiving a thermal unit 16. The body wrap 11A includes long connecting means 18 which has a left section 18A and a right section 18B. The left section 18A is here shown to include upper left ear 20; and right section 18B is shown to include upper right ear 22. The long connecting means 18 functions to extend about selected portions of the body of a patient and for attaching the upper portion 24 of the therapy section 12 to the body of the patient as hereinafter described.

The body wrap 11A also includes short connecting means 26 that has a left section 26A and a right section 26B which is here shown to include the lower left ear 28 and the lower right ear 30. The short connecting means 24 also functions to extend about the selected portions of the body of a patient and for attaching the lower portion 32 of the therapy section 12.

Figure 2:
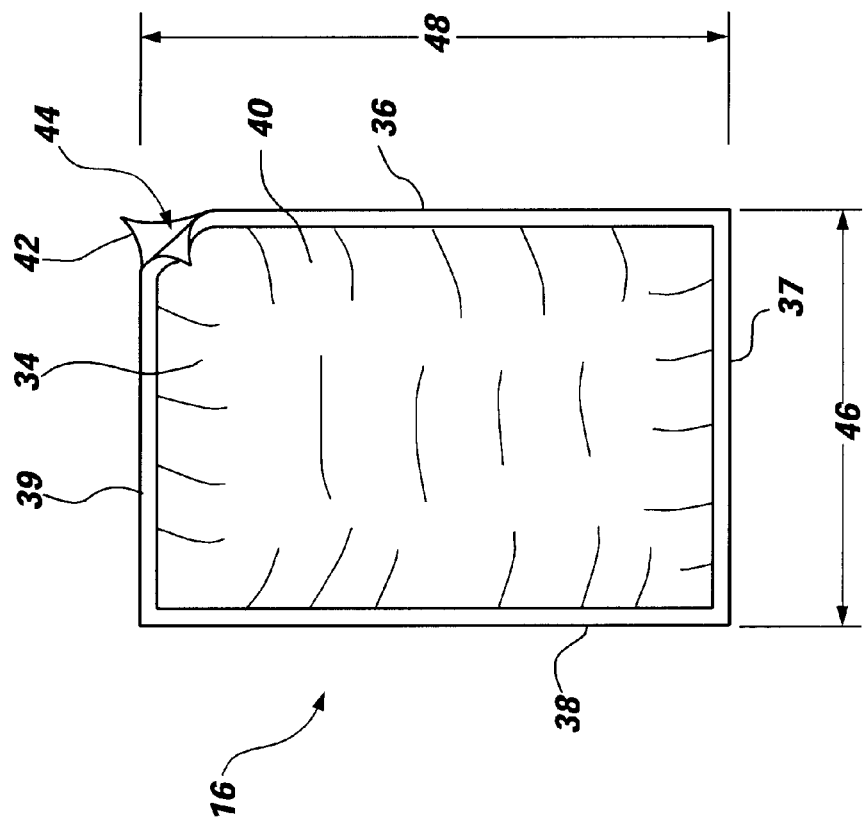
FIG. 2 is a perspective view of a thermal unit for use with the therapy wrap of the present invention.

The thermal unit 16 may be any suitable device to provide heat or cold therapy as desired. For example, an appropriately sized ice bag may be suitable. A small sealable plastic bag with ice cubes could also be suitable. Alternately, a small hot water bottle may be used. FIG. 2 illustrates a preferred thermal unit 16 which has a container 34 made of two flexible or pliable plastic sheets 40 and 42 which are joined together along their perimeters (e.g., heat sealed) to form edges 36, 37, 38 and 39. The interior 44 of the container 34 is filled with a material selected to be heated to be a source of heat therapy and also to be cooled to be a source of cold therapy. The container 34 illustrated in FIG. 2 is sometimes referred to as a gel pack which may be heated in a microwave oven or cooled in a household freezer. Although a wide range of thermal units may be suitable, at present a gel pack offered by Northland Gel-Ice Inc., Burnaby, British Columbia, Canada, Product Code 0710, is preferred. As can be seen in FIG. 2, the container 34 is sized to be rectangular in projection with a width 46 and a length 48 selected so that the container 34 may be easily inserted into the pocket 14 (FIG. 1). The container 34 may be formed into other shapes as desired so long as they may be placed in the provided pocket 14 or held to the therapy section 12 by other suitable means as hereinafter discussed. The thermal unit 16 may also be a sealed flexible container with selected chemicals which give off heat when mixed.

Referring back to FIG. 1, the therapy section 12 is depicted as the portion or section encompassed by dotted lines for illustration and discussion. The therapy section 12 reflects that part of the body wrap 11A to which the outer pocket material 50 is attached to form the pocket 14. It may be of any desired shape. That is, in projection, the pocket 14 may be rectangular, circular, ovular, triangular, hexagonal or any other geometric form or shape so long as it fits about the body of the user and functions to hold and to receive the thermal unit 16 so that the thermal therapy may be applied as desired by the user.

The pocket 14 is formed by the outer pocket material 50 and the therapy section 12 itself. The pocket 14 has a width 52 and a length 54 selected to removably receive a thermal unit 16. The width 52 and the length 54 are also selected to embrace or surround a desired portion of a selected portion of the body of a patient such as a substantial portion of the thigh or some other limb of the body. That is, the width 52 may be from about 5 inches to about 10 inches and is preferably about 7 inches. Similarly, the length 54 of the pocket 14 may be from about 7 inches to about 12 inches and is preferably about 9.5 inches. Thus, a surface area of the body to receive thermal therapy is from about 35 square inches to about 120 square inches and preferably is about 60 square inches. The pocket of FIG. 1 is preferably formed of an elastically deformable material and more preferably of a biaxially deformable material such as LYCRA™. Alternate materials may also be used if elastically deformable comparable to the therapy section 12.

Figure 3:
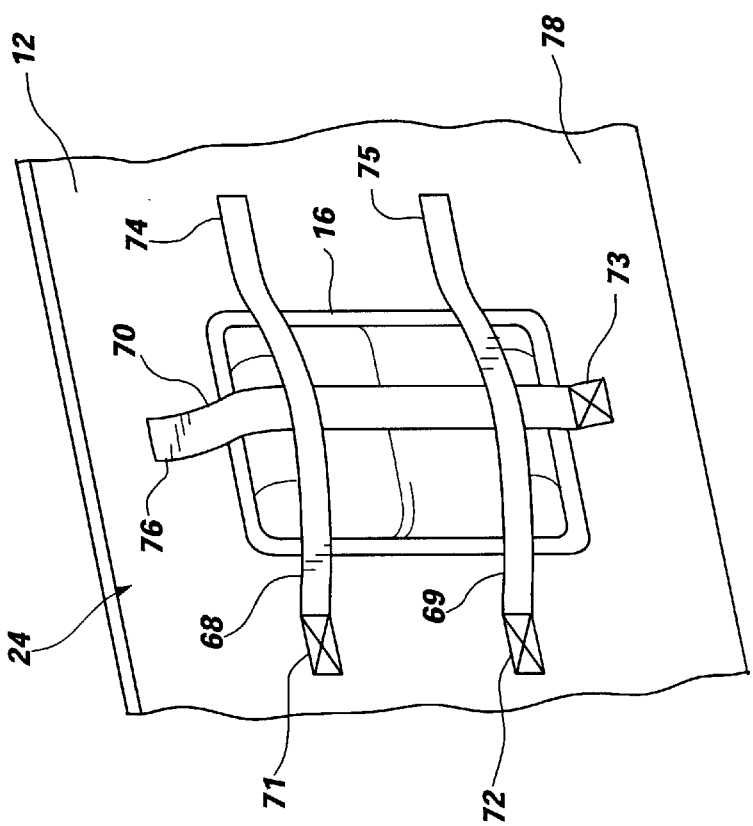
FIG. 3 is a partial perspective depiction of a therapy section of the therapy wrap of the present invention with alternate holding means to hold a thermal unit in place.

The pocket 14 is presently the preferred holding means to retain the thermal unit 16 in place relative to the therapy section 12 for placement about the body of the user. Other suitable holding means may be used if desired. For example, FIG. 3 depicts therapy section 12 in perspective with straps 68, 69 and 70. Each strap 68–70 has one end 71, 72 and 73 respectively secured to the therapy section 12 by any suitable means such as stitching as shown. The unsecured ends 74, 75 and 76 have a hook portion of a hook and pile fastening or connecting system with the pile portion attached to the therapy section 12. When the therapy section 12 is formed of laminated closed-cell neoprene as discussed hereinafter, the pile portion may be the surface material 78 laminated to the closed-cell neoprene. In lieu of the hook and pile fastener or connecting system, snaps, buttons or the like may be used to effect the desired connection. It should be understood the number of straps used is discretionary so long as the thermal unit 16 is held in place during use. One width strap, such as strap 68, and one height strap, such as strap 70, are presently believed to be the minimum number of straps necessary to retain a thermal unit 16 in place. Additional straps may be used as desired to stabilize the thermal unit 16 in place.

Figure 4:
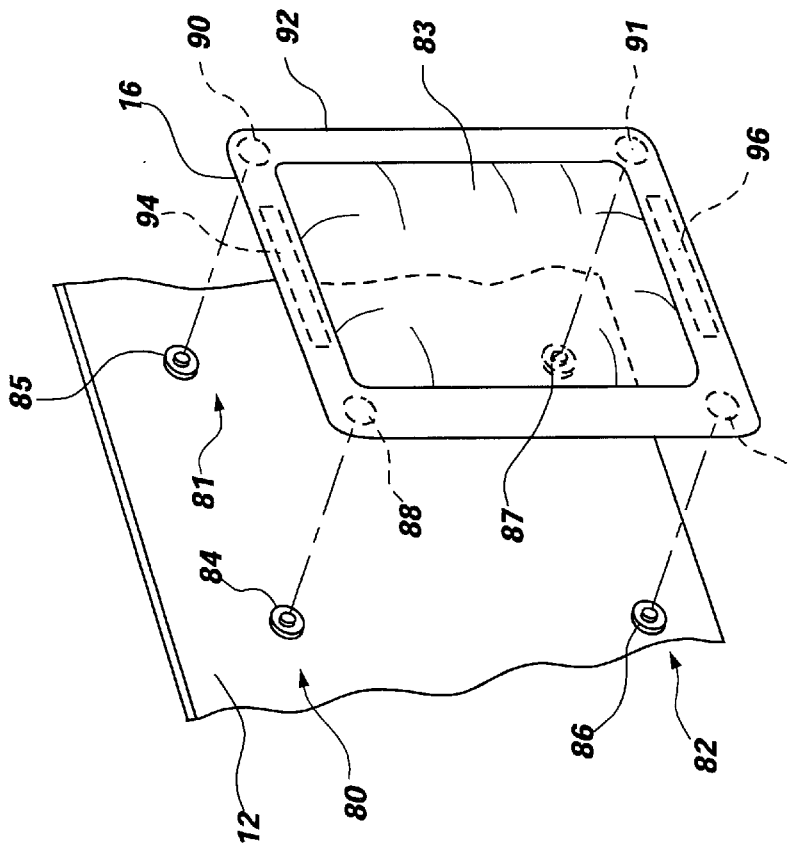
FIG. 4 is a partial perspective depiction of a therapy section of the therapy wrap of the present invention with other alternate holding means to hold a thermal unit in place.

FIG. 4 illustrates a therapy section 12 with conventional snaps 80, 81, 82 and 83 having snap insert portion 84, 85, 86 and 87 secured to the therapy section 12 by glueing or by stitching. The snap insert portions 84–87 register with corresponding snap receptacle portions 88, 89 90 and 91 glued or otherwise attached to the thermal unit 16 about its outer edges 92. Thus the thermal unit 16 may be held to the therapy section 12 by snapping the snap insert portions 84–87 into the snap receptacle portions 88–91. FIG. 4 also shows in phantom, an upper hook portion 94 and a lower hook portion 96 of a hook and pile connecting system in which the inner material of the neoprene functions as the pile portion. Thus a thermal unit 16 may be positioned on and held to the therapy section 12 by a hook and pile connector system without the pocket 14 and without conventional snaps 80–83.

Notably, the therapy section 12 is here described to have an upper portion 24 and a lower portion 32. It should be understood that the terms "upper" and "lower" are used merely for convenience to distinguish the opposite ends of the therapy section 12. Similarly "left" and "right" are selected for convenience in description to distinguish between opposite sides or spaced-apart sides of the therapy section 12. The therapy section 12 is also shown by dotted line to be rectangular in projection because the body wrap 11A is unitarily formed with the long connecting means 18 and the short connecting means 26. The terms "long" and "short" are also used to distinguish between one connecting arrangement proximate the upper portion 24 and one connecting arrangement proximate the lower portion 32. In preferred arrangements one connecting arrangement is sized to be shorter than the other. However it should be understood that the "long connecting means" and the "short connecting means" could be of virtually if not exactly identical length and be fully operative.

It should also be understood that reference herein to a "hook and pile" connector system refers to various removable connecting systems modeled after and including VEL-CRO® fastening systems now available and known to those skilled in the art.

The long connecting means 18 is the connecting arrangement for the upper portion 24 of the therapy section 12 and is here shown to be unitarily formed with the upper portion 24 of the therapy section 12 with the left section 18A being formed as the left ear 20 and the right section 18B being formed as the right ear 22. The left section 18A and the right section 18B could be any size or shape desired. However, the "ear" shape shown in FIG. 1 is preferred because it may, in some applications, increase the external insulation while providing more surface area for connecting. The ear shape also provides a larger area to act as handles for pulling the wrap section 11 about the patient or otherwise positioning the wrap section 11. Since some users may be infirm, a large handle size facilitates use. For example, the width or first distance 58 of the ear and the average or effective height 59 may be about three inches to provide sufficient material to easily grasp and pull.

It should also be noted that the first distance 58 and the second distance 60 of the left section 18A and the right section 18B are selected so that the width 53 of the therapy section and the total width 62 permits and facilitates use as depicted in FIGS. 6–16 as discussed hereinafter.

Figure 5:
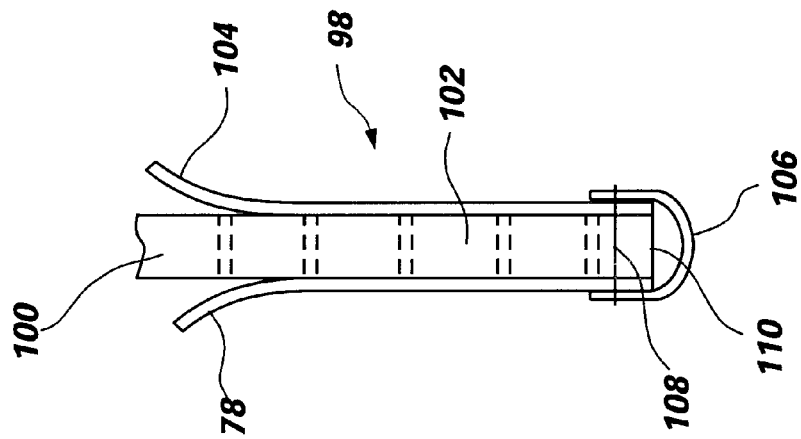
FIG. 5 is a partial cross sectional view of laminated closed-cell neoprene for use with the present invention.

In use it has been found that preferred material is a closed-cell neoprene which is elastically deformable. FIG. 5 is a cross sectional view of an alternate laminated closed-cell neoprene 98 which could be used to form the therapy wrap 10. Alternate materials may be used which are elastically deformable and particularly those that are biaxially elastically deformable. In FIG. 5, the closed-cell neoprene 100 is shown substantially enlarged for clarity of illustration and differs from the preferred closed-cell neoprene only in that it has a plurality of apertures or holes 102 formed in it. The plurality of apertures or holes 102 may be formed through the neoprene 100 to facilitate the transmission of air and moisture therethrough. A first material or outer material 104 is laminated to the neoprene 100 to form an outer surface. The first material 104 is preferably a polyester material which is VELCRO® compatible or a VELCRO® mate material which is formed to function as the pile portion of a hook and pile connecting system like a VELCRO® hook and pile system. More particularly, the first material 104 functions as the pile portion for connection to the hook portions such as the first attaching element 64 of the long connecting means 18, the first attaching element 121 of the short connection means and other hook portions identified or discussed herein. The second material or inside material 78 is also preferably a polyester material which is a VELCRO® mate material or VELCRO® compatible to function as the pile portion of a hook and pile system such as or comparable to a VELCRO® hook and pile system. Material 78 therefore can function with the several hook portions of hook and pile connecting arrangements discussed herein. Lamination of the first or outside material 104 and the inside material 78 is effected by any conventional or suitable means. With the first material 104 and the second material 78 compatible to function as a pile portion of a hook and pile portion of a hook and pile connector system, it can be seen that the wrap 10 effectively becomes infinitely adjustable and susceptible to connection to the body in a number of useful configurations particularly with the use of the long and short connecting means as hereinbefore discussed.

FIG. 5 also shows piping 106 stitched 108 along the outer edge 110 of the illustrated laminated closed-cell neoprene 98. The piping 106 may be applied along the outer edges of the therapy section 12, lower ears 28 and 30 and upper ears 20 and 22 to enhance the appearance and to reduce or limit potential delamination of the first material 104 and the inner material 78.

The left section 18A and the right section 18B of the long connecting means 18 are preferably formed in the shape of ears and in turn are the left ear 20 and the right ear 22. The left ear 20 and right ear 22 may function as insulation and in turn to retain heat when overlapped over the therapy section 12. The left ear 20 and the right ear 22 may also function to provide additional support to the body in the area where therapy is to be applied. That is, thermal therapy is often desired in locations in which an individual may have anything from sore muscles to injured ligaments, injured cartilage, sprains, torn muscles, broken bones and other injuries. Additional mechanical support in the afflicted region may be found to be helpful for some patients. Tensional placement may be found to be helpful by providing mechanical support while trapping body heat for thermal therapy. The left ear 20 and the right ear 22 also have increased surface area in relation to narrow straps often found in the art and in turn function as handles for easier grasping by users particularly users who are infirm or disabled.

As shown the left ear 20 and the right ear 22 extend outwardly a first length 58 and a second length 60 respectively. The first length 58 and the second length 60 are selected so that in combination with width 53 of the therapy section 12, the total length 62 of the body wrap 11A is sufficient to encompass or to be wrapped around, for example the largest diameter of a limb of the user such as the upper area of the thigh of a typical user (see FIG. 10). Preferably the first length 58 and the second length 60 are equal in length. However, they need not be equal.

The long connecting means 18 has long attaching means comprised of a first attaching element 64 attached to or formed with the left section 18A and more specifically the upper left ear 20 and a second attaching element 66 attached to or formed with the right section 18B and more specifically the upper right ear 22. The long attaching means 18 functions so the user may attach the left section 18A and the right section 18B together and in particular so the user may attach the upper left ear 20 and the upper right ear 22 together. With the therapy section 12 positioned in a desired location on the body, the upper left ear 20 and the upper right ear 22 may be pulled to wrap the therapy section 12 thereabout and to position the upper left ear 20 and the upper right ear 22 relative to each other so that the attaching element 64 and the attaching element 66 are positioned for the attachment of one to the other to hold the therapy section 12 in place to apply thermal therapy from the thermal unit 16 and, if desired, compressive therapy to the desired location on the body.

In preferred applications, the attaching element 64 is the hook portion 65 of a hook and pile type connecting system or arrangement; and the attaching element 66 is the pile portion of a hook and pile type connecting system. As presently configured, the upper left ear 20 and the upper right ear 22 are formed unitarily with the therapy section 12 all of closed-cell neoprene with the inner material 78 and the first or outer material 104 both selected to function as the pile portion of the hook and pile connector system as discussed with reference to FIG. 5. Thus, a separate pile portion of a hook and pile connector system need not be provided and attached, though in some applications, such may be desired. With the hook portion 65 attached to either the upper left ear 20 as shown, or optionally to the upper right ear 22, the user may fasten the long attaching means of the long connecting means 18 to the body of a user to hold the thermal unit 16 in place and with tension, if desired.

The left section 26A and the right section 26B of the short connecting means 26 are also preferably formed in the shape of ears and in turn are the lower left ear 28 and the lower right ear 30. As so formed, the lower left ear 28 and the lower right ear 30 have an effective surface area that in some applications or uses assists in the ability to grasp, in the ability to apply compressive therapy and also in the ability to act as insulation and in turn to retain heat or cold when overlapped over the therapy section 12 much the same as the upper left ear 20 and the upper right ear 22. The lower left ear 20 and the lower right ear 22 may also function to provide additional support to the body in the area where therapy is to be applied as noted hereinbefore. Additional support in that region may be found to be helpful for some patients. Of course the lower left ear 20 and the lower right ear 22 may also function as handles for the user and may function as part of a hook and pile connector system much the same as the upper left ear 20 and upper right ear 22.

As shown the lower left ear 28 and the lower right ear 30 extend outwardly a third length 124 and a fourth length 126 respectively. The third length 124 and the fourth length 126 are selected so that in combination with the therapy section 12, the total length 128 at the bottom section of the therapy section 12 and the body wrap 11A is sufficient to encompass or to be wrapped around, for example, a limb of the user spaced from the long connecting means 18 a distance 54 as can be seen in FIG. 1. Thus the long connecting means 18 may be positioned about the upper thigh, for example, and the short connecting means 26 about a lesser diameter or lesser perimeter or circumference of the thigh (see FIG. 10). Although the first length 124 and the second length 126 are selected to be equal, they need not be equal. Further, the therapy section 12 and the body wrap 11A have a height 127 as well as a width 62 selected so that the body wrap 11A may be used in multiple locations rather than in one or two. That is, wraps are not known to be available for a wide range of multiple uses as herein provided.

The short connecting means 26 has short attaching means comprised of a first attaching element 120 attached to or formed with the left section 26A and more specifically the lower left ear 28. The short connecting means 26 also has a second attaching element 122 attached to or formed with the right section 26B and more specifically the lower right ear 30. The short connecting means 26 functions so the user may attach the left section 26A and the right section 26B together and in particular so the user may attach the lower left ear 28 and the lower right ear 30 together to form an opening for the limb of a user. The opening may be varied in size or cross section. However, the maximum size or cross section is preferably less than the maximum size or cross section formable by joining the upper right ear 20 and the upper left ear 22. The short connecting means 26 thereby uses less material so that the body wrap 11A fits more comfortably about the several limbs of the user.

With the therapy section 12 positioned in a desired location on the body, the lower left ear 28 and the lower right ear 30 may be pulled by the user to wrap the therapy section 12 about the desired location and to position the lower left ear 28 and the lower right ear 30 relative to each other. In turn, the attaching element 120 and the attaching element 122 are positioned for the attachment of one to the other to hold the therapy section 12 in place for the application of thermal therapy to the desired location on the body. The ears 20, 22, 28 and 30 may also be pulled tight enough to apply tensional therapy with or without the application of thermal therapy.

In preferred applications, left attaching element 120 is the hook portion 121 of a hook and pile type connecting system; and the right attaching element 122 is the pile portion of the hook and pile type connecting system or arrangement. The first attaching element 120 may be the pile portion; and the attaching element 122 may be the hook portion, if desired.

As presently configured, the lower left ear 28 and the lower right ear 30 are each formed unitarily with the therapy section 12 all of closed-cell neoprene with the inner material 78 and the first material 104 or outer material both selected to function as the pile portion of the hook and pile connector system. Thus, a separate pile portion of a hook and pile connector system need not be provided. With the hook portion attached to either the lower left ear 28 or the upper right ear 30, the user may fasten the short attaching means to the body of a user to hold the thermal unit 16 in place and with tension, if desired.

In FIG. 1, the first strap 11B is strap 56 which is shown to have a first end 130 and a second end 132. Strap attaching means are provided at or proximate the first end 130 and the second end 132 for attaching the first end 130 and the second end 132 together and for attaching the first end 130 and the second end 132 to the long attaching means and to the short attaching means as discussed hereinafter.

The strap attaching means has a first attaching element 134 and a second attaching element 136 formed for attaching one to the other. The illustrated strap 56 is formed out of the same laminated closed-cell neoprene material as the therapy section 12, the long connecting means 18 and the short connecting means 26. In turn, the outer surfaces 138 and 140 of the strap function as the pile portion of a hook and pile attaching or connecting system. With the first attaching element 134 being the hook portion of the hook and pile connecting system attached, it can be seen that the strap 56 may be wrapped about something with the first attaching element 134 attaching to the second element 136 to hold the strap 56 snugly in place and to apply tension by pulling on the strap 56 to place it in tension, if desired. The strap 56 is sized in length 142 (e.g., 24 inches) to extend from either the long attaching means 18 and short attaching means 26 about the body to hold the therapy section 12 in desired locations as more fully discussed hereinafter.

The strap 56 may also be attached to either the long attaching means 18 or to the short attaching means 26. It can be seen that the hook portion 65 of the long attaching means 18, the hook portion 121 Of the short attaching means 26, and the hook portion 134 of the strap 56, may be interconnected with the pile portion of the therapy section 12 which is the entire outer surface 104 and inner surface 78 of the body wrap 11A or to the pile portion 67 of the long connecting means 18, the pile portion 123 of the short connecting means 26 and outer surface and inner surface 138, 140 of the strap 56 to effect different combinations of connections about selected body portions as hereinafter discussed.

FIG. 6 shows a body wrap 148 comparable to body wrap 11A positioned about the ankle 150 of a user between the lower leg 152 and the foot 154. Specifically, the wrap 148 is made of closed-cell neoprene with polyester materials laminated thereto as hereinbefore described with respect to FIG. 5. The wrap 148 is configured with an upper left ear 156 having the hook portion of the hook and pile connector system the same as depicted in FIG. 1. However the short connecting means of the body wrap 148 has a lower right ear 158 with the hook portion of the hook and pile connecting system secured thereto to attach to the outer material 160 which is comparable to outer or first material 104. Thus the wrap 148 may be used with the upper right ear 162 tucked under the upper left ear 156 and the lower left ear 164 tucked under the lower right ear 158. In use, one may hold ear 162 while pulling on ear 156 to apply tension for effecting a snug connection and even tensional therapy. Similarly, one may hold the ear 164 and pull on ear 158 to effect a connection and also to apply tensional therapy if desired. Tensional therapy may be applied in lieu of and in addition to thermal therapy when the thermal unit 16 is placed in or attached by the holding means and more specifically the pocket 14. The user may determine the degree of desired tension by pulling on the upper left ear 156 and the lower right ear 158.

Figure 8:
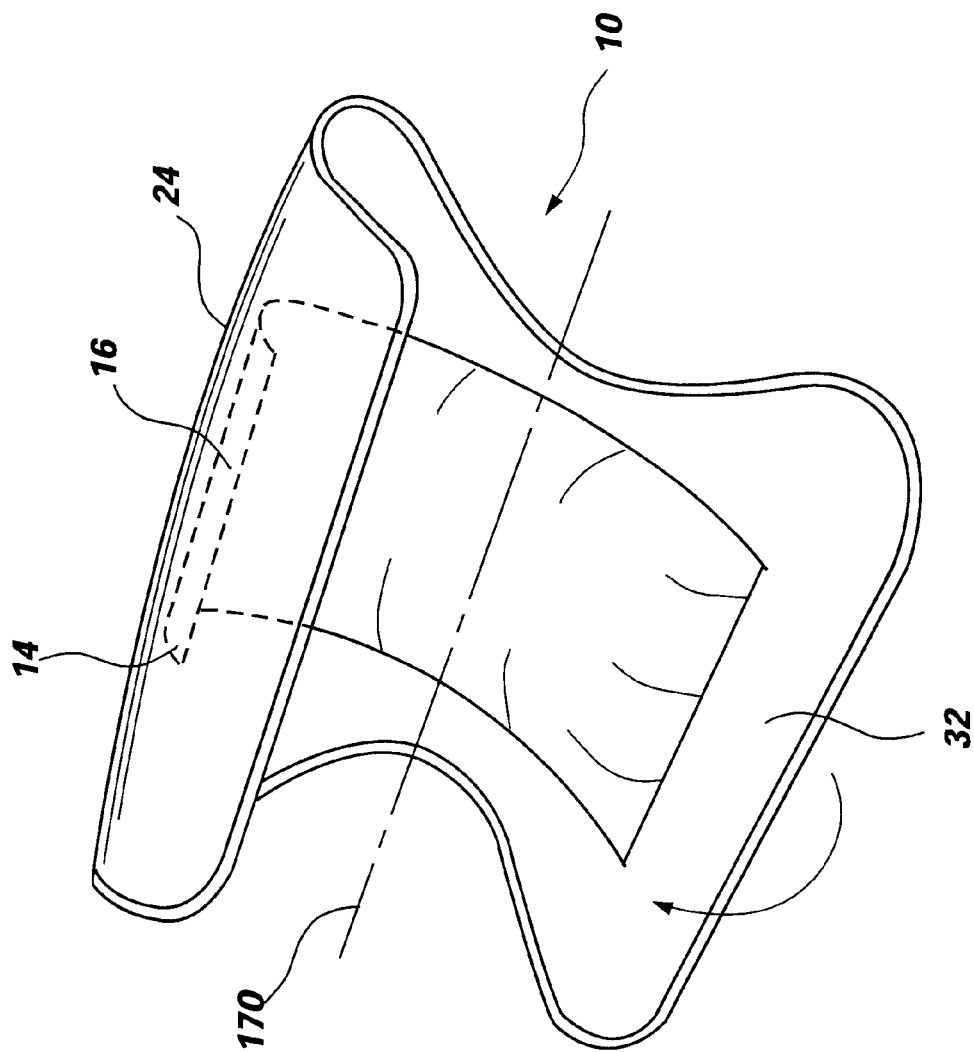
FIG. 8 is a perspective of the therapy wrap of the present invention being configured for placement about the neck of a user.

FIGS. 7 and 8 show a body wrap 11A of FIG. 1 applied to the neck of a user. To place about the neck, a thermal unit 16 such as a gel pack or other pliable and deformable device configured to provide heat or cold therapy is placed in the pocket 14 or held in place by other holding means. Thereafter, the upper section 24 is rolled over and down toward a mid line 170. Similarly the lower section 32 is rolled up toward the mid line 170. When rolled, the height 172 (FIG. 7) is that which the user desires. To secure the body wrap 11A in place, the user wraps the strap 56 about body wrap 11A which is positioned about the neck. The first end 130 and the second end 132 of the strap 56 are then attached to each other with the strap 56 in tension to hold the body wrap 11A in place without interfering with the patient's breathing. The strap 56 also may be connected to long attaching means or the short attaching means to secure the body wrap 11A about the neck. Hot or cold therapy is thus applied to the neck to address, for example, a "stiff neck" or other neck injury.

Figure 9:
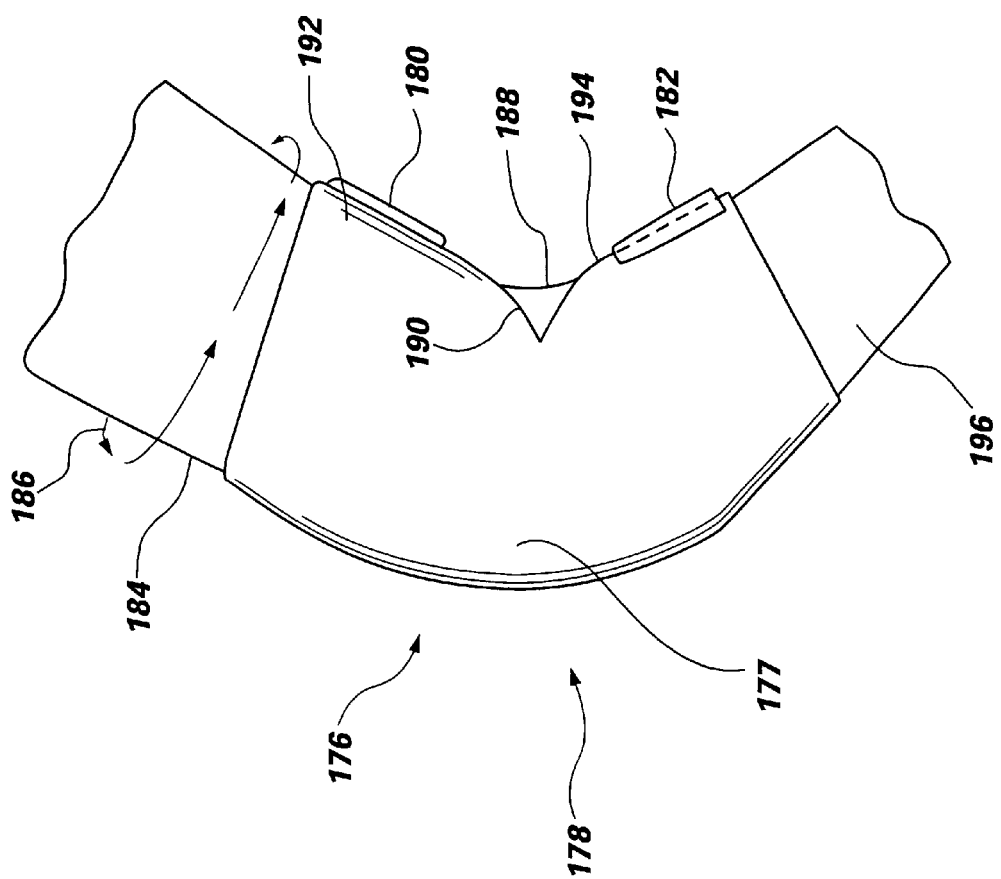
FIG. 9 is a depiction of the therapy wrap of the present invention positioned about the knee of a user.
Figure 11:
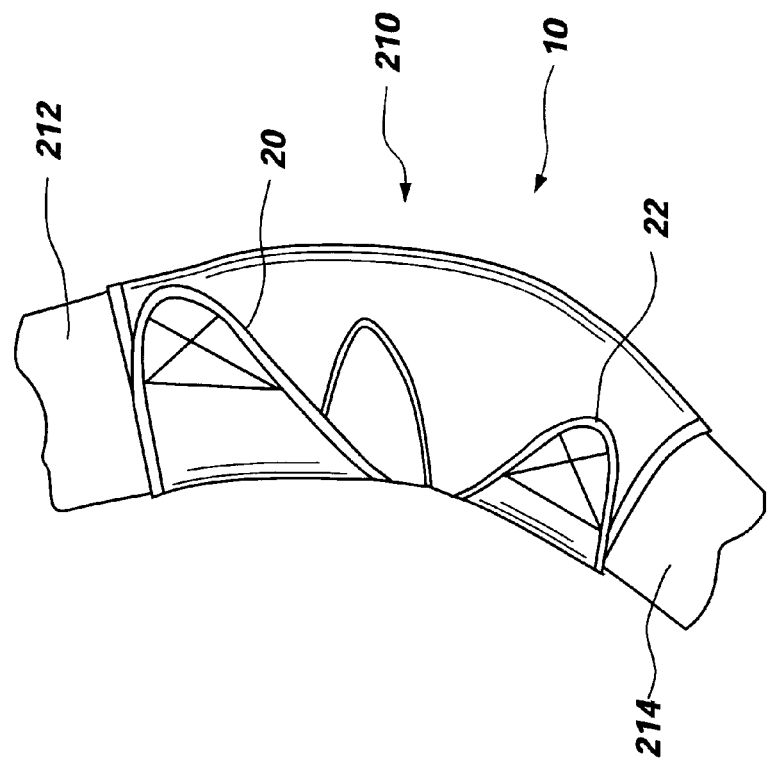
FIG. 11 is a depiction of the therapy wrap of the present invention positioned about the elbow of a user.

FIG. 9 shows a therapy wrap 176 positioned about the knee 178 of the user. The therapy wrap 176 differs from the body wrap 11A of FIG. 1 only in that the upper right ear 180 and the lower right ear 182 have the hook portion of hook and pile connecting system rather than the upper left ear 20 and the lower left ear 28 as shown in FIG. 1. It should be noted that the upper attaching elements and lower attaching elements are formed comparable to ears 20, 22, 28 and 30. With the wrap 176 formed into what may be considered an hour-glass type shape as best seen in FIG. 1, the wrap 176 can be positioned to extend around the circumference or perimeter 186 of the upper leg 184 and form a notch or opening 190 proximate the back 188 of the knee 178. Material is thus not behind the knee 178 avoiding bunching during flexion and the associated discomfort from bunching material. In turn, the wrap 176 is easy to use and comfortable to wear when applied at the knee.

To apply the wrap 176, the user first inserts a thermal unit 16 at a desired temperature into the pocket 14. The therapy section 177 is then placed at the desired location on or about the knee 178. The upper right ear 180 and upper left ear 192 are drawn about the upper leg 184 and attached one to the other applying tensional forces if desired. The lower left ear 194 and lower right ear 182 are similarly drawn about the lower leg 196 just below the knee 178 and secured to each other to secure the therapy unit 176 in place. The strap 56 may be wrapped about the wrap 176 to further hold it in place and to increase the tensional forces if desired.

Figure 10:
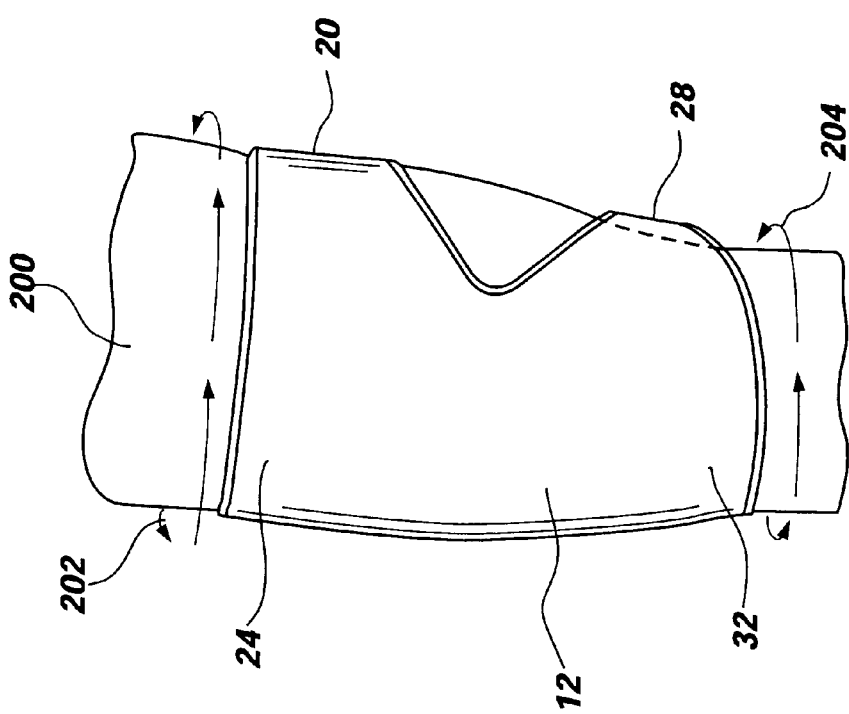
FIG. 10 is a depiction of the therapy wrap of the present invention positioned about the thigh of a user.
Figure 12:
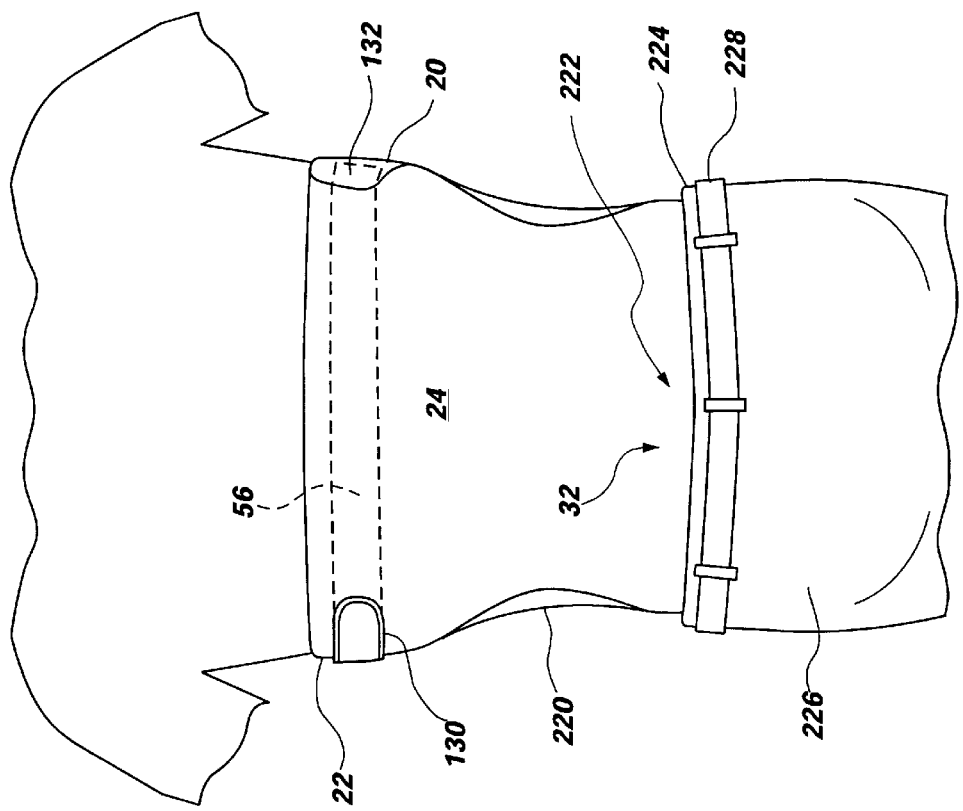
FIG. 12 is a depiction of the therapy wrap of the present invention positioned about the torso of a user.
Figure 13:
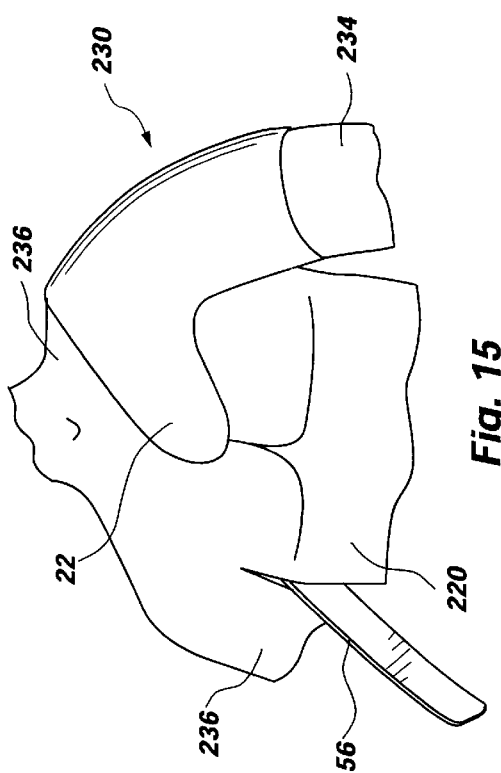
FIGS. 13–16 illustrate several steps in positioning a therapy wrap of the present invention positioned about the shoulder of a user.
Figure 14:
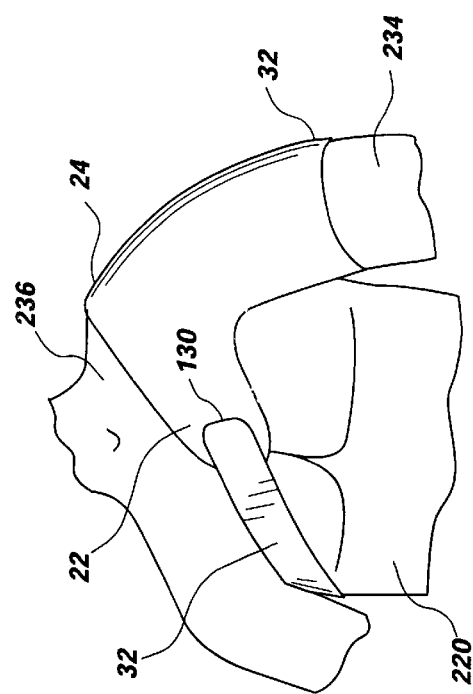
Figure 15:
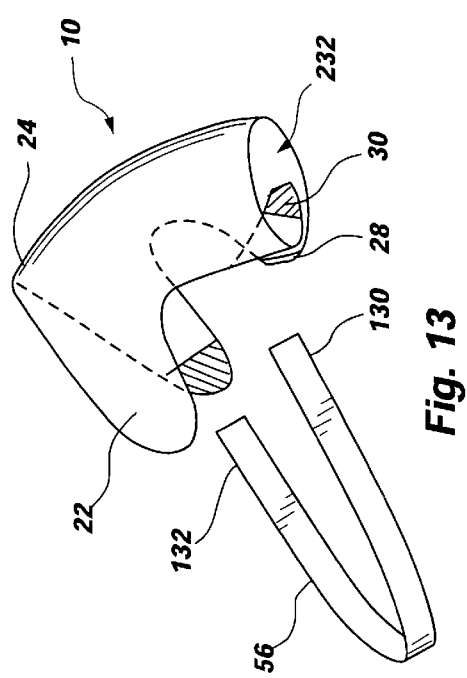
Figure 16:
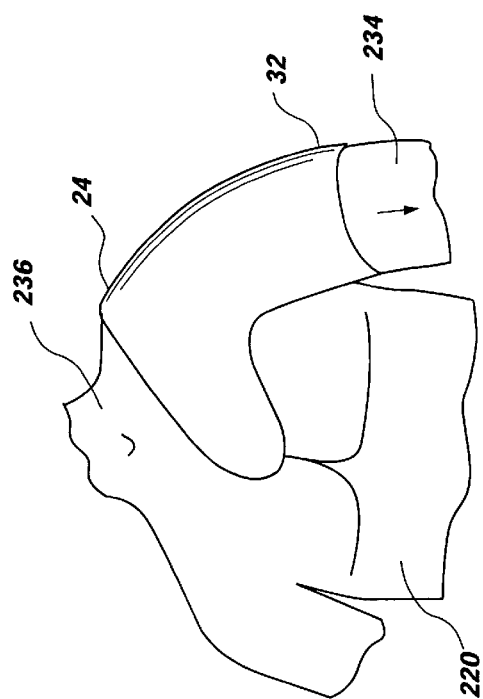

FIG. 10 shows the body wrap 11A of FIG. 1 positioned about the thigh 200 of a user. A thermal unit 16 properly cooled or heated is placed in the pocket 14. The therapy section 12 is then placed on the thigh 200 in the desired location. Thereafter, the upper left ear 20 and the upper right ear 22 are drawn about the thigh 200 proximate the larger diameter or perimeter 202. The lower left ear 28 and the lower right ear 30 are drawn about the thigh 200 spaced away from the upper portion 24 with a perimeter 204 somewhat less than the upper perimeter 202. The user may wrap the strap 56 thereover for additional strength or tension if desired. Alternately, for users who have a thigh 200 with perimeters 202 and 204 so large that the upper left ear 20 and upper right ear 22 cannot be secured to each other and enjoy a comfortable installation, the user may select the strap 56 to wrap about the body wrap 11A to effect installation. Installation along other parts of the leg such as the calf is similarly effected.

The body wrap 11A may also be placed about the elbow 210 between the upper arm 212 and the lower arm 214. Here again, the user places a thermal unit 16 at a desired temperature in the pocket 14 and then secures the body wrap 11A about the elbow. The upper left ear 20 and the lower left ear 28 are positioned to attach to the outer surface or first material 104 of the respective upper right ear 22 and lower right ear 30 or the therapy section 12 to hold the wrap 10 in place as long as desired.

It can be seen that the body wrap 11A may be placed anywhere along the limbs of the user. That is, the body wrap 11A may be positioned anywhere along the length of the arms between the shoulder down to and including the wrist and from the upper thigh to the foot.

The body wrap 11A of FIG. 1 may also be placed about the torso 220 of the user. A thermal unit 16 is placed in the pocket 14. The therapy section 12 is then placed in a desired location which may be the lower back 222 or other desired therapy location. When in place as shown, the upper left ear 20 and the second end 132 of the strap 56 are attached together. The strap 56 is then extended about the chest with the hook portion 134 of the first end 130 then being attached to the upper right ear 22. To secure the lower section 32 of the therapy unit 12, a second strap is used. Here, any suitable belt-like structure available from the garments of the user is suitable and preferred. However, separating a second strap comparable to strap 56 may be provided. Thus, the lower section 32 is shown tucked into the waist band 224 of pants or trousers 226 (or the like) or optionally between the pants or trousers 226 or other garment and a belt 228 so that the user may hold the body wrap 11A and more specifically the lower section 32 in place by tightening her or his belt 228. For females, the upper section 24 may alternatively be held in place by undergarment structure (e.g., a bra) with the strap 56 used to secure the lower section 32 in a fashion similar to that described for the upper section 24.

In practice it is expected that the upper section 24 will be positioned upwardly on the torso 220 because a larger perimeter (e.g., chest measurement) is expected. The strap 56 is sized to extend between the upper left ear 20 and the upper right ear 22 of a selected patient. Patients with very large biceps by find it necessary to put the upper right ear 20 and upper right ear 22 about a bicep and use a longer strap 56 to effect a comfortable connection around the upper trunk (see FIGS. 13–16).

FIGS. 13–16 show the steps necessary to install the body wrap 11A of FIG. 1 about and on the shoulder 230 of a user. First, a thermal unit 16 at a desired temperature to provide heating or cooling is positioned in the pocket 14 of the therapy section 12. Next, the lower left ear 28 and the lower right ear 30 are secured to each other to form an arm hole 232. The second end 132 of the strap 56 is also attached to upper left ear 22 having the hook portion 65 of a hook and pile type connector. The arm 234 of the user is then positioned through the arm hole 232 with the upper section 24 positioned where desired between the neck 236 and the outer portion of the shoulder 230 so that the thermal therapy is applied to a desired location. The user then reaches behind and grasps the strap 56 which is then pulled around to be under the opposite arm 236. The first end 130 of the strap 56 is then moved across the chest and attached to the first material or outer material 104 of the upper right ear 22. The strap 56 may be tensioned as desired to apply compressive therapy as well as thermal therapy to the shoulder 230.

In use, the user may remove the body wrap 11A or its equivalent whenever the temperature is sensed to be ineffective at providing the desired therapy. Of course, the body wrap 11A may be void without a thermal unit 16 to apply compressive therapy apart from the thermal therapy provided by the thermal unit 16. When the user no longer desires the compression or the support provided by the body wrap 11A, it can be removed.

It may also be noted that the body wrap 11A of FIG. 1 may be provided in different sizes including sizes for children, women and men. The body wrap 11A may also be used on selected animals for similar purposes.

The hook portions and the pile portions of the hook and pile type connectors described herein are all sized to be compatible. That is, the laminated material 78 and the outer material 104 are all selected to effect a secure mechanical connection with a corresponding hook portion that is conveniently sized (e.g., 4–10 square inches). The hook portions (e.g., 65, 121, 134) identified must be sized to provide the desired removable connection to the pile portion which are in the preferred arrangements the entire or a substantial portion of the exterior surface areas of the body wrap 11A and the first strap 11B as hereinbefore discussed particularly in reference to FIG. 5.

It should also be noted that the upper left ear 20 and upper right ear 22 of FIG. 1 as well as the lower left ear 28 and lower right ear 30 may be provided with a hook portion comparable to hook portions 65 and 121. Increased flexibility of use is achieved while the hook portion of one of the lower left ear 28 and lower right ear 30 as well as the upper left ear 20 and upper right ear 22 will be in contact with the skin of the user in several of the applications comparable to those illustrated in FIGS. 6 and 9–16. The hook portion may be on the exterior surface 104 of both of the upper ears 20, 22 and on both of the lower ears 28, 30 in some embodiments. Further, other types of connectors may be used including snaps and hooks. Similarly, the strap 56 may have a hook portion of the hook and pile connector system at both ends 130 and 132. Attachment may nonetheless be effected by attaching the hook portion to the outer material 102 of the therapy section and similar outer material of the ears and the strap.

It is to be understood that the embodiments and methods of the inventions herein described are merely illustrative of the application of the principals of the invention. Reference herein to details is not intended to limit the scope of the claims which themselves recite those features considered to be essential to the invention.

What is claimed is:

1. A wrap for applying thermal therapy to a patient, said wrap comprising:

a therapy section having a top, a bottom, a left side and a right side, said therapy section being sized for positioning about a selected body element of a patient;

a thermal unit having a reservoir of material at a temperature selected for applying thermal therapy to the selected body element of a patient;

holding means for removably attaching and holding said thermal unit to said therapy section;

long connecting means attached to said therapy section proximate one of said top and said bottom, said long connecting means having a left section extending outwardly from said left side a first length and a right section extending outwardly from said right side a second length;

long attaching means having a first attaching element attached to or formed with said left section of said long connecting means and a second attaching element attached to or formed with said right section of said long connecting means for removably attaching said left section and said right section together to form an opening adjustable in size to receive a selected body element of a patient therein and for attaching said therapy section to said body element to cause thermal energy from said thermal unit to be applied to said body element, said first attaching element and said second attaching element being formed to interact to secure themselves together;

short connecting means attached to said therapy section proximate the other of said top and said bottom, said short connecting means having a left section extending outwardly from said left side a third length and a right section extending outwardly from said right side a fourth length, said third length and said fourth length together being less than said first length and said second length together; and short attaching means having a first attaching element attached to or formed with said left section of said short connecting means and a second attaching element attached to or formed with said right section of said short connecting means for removably attaching said left section of said short connecting means and said right section of said short connecting means together to form an opening adjustable in size for positioning about the selected body element of a patient spaced from said long connecting means and for attaching said therapy section to said body element to cause thermal therapy from said thermal unit to be applied to said body element, said first attaching element and said second attaching element being formed to interact to secure themselves together.

2. A wrap for applying thermal therapy to a patient, said wrap comprising:

a therapy section having a top, a bottom, a left side and a right side, said therapy section being sized for positioning about a selected body element of a patient;

a thermal unit having a reservoir of material at a temperature selected for applying thermal therapy to the selected body element of a patient;

holding means for attaching and holding said thermal unit to said therapy section;

long connecting means attached to said therapy section proximate one of said top and said bottom, said long connecting means having a left section extending outwardly from said left side a first length and a right section extending outwardly from said right side a second length;

long attaching means having a first attaching element attached to or formed with said left section of said long connecting means and a second attaching element attached to or formed with said right section of said long connecting means for removably attaching said left section and said right section together to form an opening adjustable in size to receive a selected body element of a patient therein and for attaching said therapy section to said body element to cause thermal energy from said thermal unit to be applied to said body element, said first attaching element and said second attaching element being formed to interact to secure themselves together;

short connecting means attached to said therapy section proximate the other of said top and said bottom, said short connecting means having a left section extending outwardly from said left side a third length and a right section extending outwardly from said right side a fourth length, said third length and said fourth length together being less than said first length and said second length together;

short attaching means having a first attaching element attached to or formed with said left section of said short connecting means and a second attaching element attached to or formed with said right section of said short connecting means for removably attaching said left section of said short connecting means and said right section of said short connecting means together to form an opening adjustable in size for positioning about the selected body element of a patient spaced from said long connecting means and for attaching said therapy section to said body element to cause thermal therapy from said thermal unit to be applied to said body element, said first attaching element and said second attaching element being formed to interact to secure themselves together; and a strap having a strap length, a strap first end, a strap second end and strap attaching means proximate said strap first end and said strap second end for removable connection to each other and for removable connection to one of said first element and said second element of said long attaching means and to one of said first element and said second element of said short attaching means to extend about a selected body element.

3. The therapy wrap of claim 2 wherein said long connecting means, said short connecting means and said strap are formed from an elastically deformable material.

4. The therapy wrap of claim 3 wherein said holding means is a pocket sized to removably receive said therapy unit therein.

5. The therapy wrap of claim 4 wherein said first attaching element and said second attaching element of said long attaching means are one and the other of the hook and pile of a hook and pile connector, wherein said first attaching element and said second attaching element of said short attaching means are one and the other of the hook and pile of a hook and pile connector, and wherein said strap attaching means is a hook and pile connector having the hook portion at the first end and the pile portion at the second end of said strap.

6. The therapy wrap of claim 5 wherein said first length and said second length are equal.

7. The therapy wrap of claim 6 wherein said third length and said forth length are equal.

8. The therapy wrap of claim 7 wherein said first attaching element and said second attaching element of said long attaching means and said first attaching element and said second attaching element of said short attaching means are made of a base material having a first surface and a second surface in substantial alignment with a first exterior material laminated to one of said first surface and said second surface, said first exterior material being formed to function as the pile of a hook and pile connector.

9. The therapy wrap of claim 8 wherein said base material is a closed-cell, neoprene material, and wherein the other of said first surface and said second surface has a second material laminated thereto which functions as the pile portion of a hook and pile connector.

10. The therapy wrap of claim 9 wherein said therapy section is formed of a closed-cell neoprene material having a first surface and a second surface opposite said first surface, said first surface having a first exterior material laminated to one of said first surface and said second surface and a second exterior material laminated to the other of said first surface and said second surface, said first exterior material and said second exterior material being formed to function as the pile portion of a hook and pile connector.

11. The therapy wrap of claim 10 wherein said pocket is formed from a thin elastic material stitched to one of said first surface and said second surface of said therapy section.

12. A method of applying thermal therapy to a patient, said method comprising:

providing a wrap having a therapy section with a top, a bottom, a left side and a right side, said therapy section being sized for positioning about a selected body element of a patient, a thermal unit having a reservoir of material at a temperature selected for applying thermal therapy to the selected body element of a patient, holding means attached to said therapy section for removably attaching and holding said thermal unit to said therapy section;

long connecting means attached to said therapy section proximate one of said top and said bottom, said long connecting means having a left section extending outwardly from said left side a first length and a right section extending outwardly from said right side a second length, long attaching means having a first attaching element attached to or formed with said left section of said long connecting means and a second attaching element attached to or formed with said right section of said long connecting means for removably attaching said left section and said right section together to form an opening adjustable in size to receive a selected body element of a patient therein and for attaching said therapy section to said body element to cause thermal energy from said thermal unit to be applied to said body element, said first attaching element and said second attaching element being formed to interact to secure themselves together, short connecting means attached to said therapy section proximate the other of said top and said bottom, said short connecting means having a left section extending outwardly from said left side a third length and a right section extending outwardly from said right side a fourth length, said third length and said fourth length together being less than said first length and said second length together, and short attaching means having a first attaching element attached to or formed with said left section of said short connecting means and a second attaching element attached to or formed with said right section of said short connecting means for removably attaching said left section of said short connecting means and said right section of said short connecting means together to form an opening adjustable in size for positioning about the selected body element of a patient spaced from said long connecting means and for attaching said therapy section to said selected body element to cause thermal therapy from said thermal unit to be applied to said body element, said first attaching element and said second attaching element being formed to interact to secure themselves together;

removably attaching said thermal unit to said therapy section with said holding means;

positioning said therapy section at a position against and about said selected body element of a patient;

manipulating said long connecting means and said short connecting means about said selected body element to position said therapy section snugly against said selected body element;

positioning said left section and said right section of said long connecting means proximate each other;

urging said first attaching element and said second attaching element of said long attaching means together to removably fasten said first attaching element to said second attaching element;

positioning said left section and said right section of said short connecting means proximate each other; and urging said first element and said second element of said short attaching means together to removably fasten said first attaching element to said second attaching element.

13. The method of claim 12 wherein said therapy section is formed to have one surface that is the pile portion of a hook and pile connecting system, wherein said first element and said second element of said long attaching means are one of the hook portion and the pile portion of a hook and pile connecting system, and wherein said first element and said second element of said short attaching means are one of the hook portion and the pile portion of a hook and pile connecting system.

14. The method of claim 13 further including:
providing a strap having a strap length, a strap first end, a strap second end and strap attaching means having a hook portion of a hook and pile connecting system proximate said strap first end and a pile portion of a hook and pile connecting system proximate said strap second end;
positioning said strap about said wrap;
removably connecting said hook portion of said strap attaching means to one of said pile portion of said strap attaching means, said pile portion of said long attaching means, said pile portion of said short attaching means and the pile portion of the therapy section surface and removably connecting said pile portion of said strap attaching means to one of the hook portion of said strap attaching means, the hook portion of said long attaching means and the hook portion of said short attaching means.

15. The method of claim 14 wherein said therapy section, long connecting means and short connecting means are made of a closed-cell neoprene material with a surface material laminated to one of its opposite outside surfaces, said surface material being selected to function as the pile element of a hook and pile connecting system.

16. The method of claim 15 wherein said selected body element is one of a knee, thigh, ankle, calf, upper arm, lower arm and neck.

17. The method of claim 14 wherein said holding means is a pocket formed on said therapy section sized to removably receive said thermal unit.

18. A method of applying thermal therapy to a patient, said method comprising:
providing a wrap having
a therapy section with a top, a bottom, a left side and a right side, said therapy section formed of an elastically deformable material and being sized for stretching about a selected body element of a patient,
a thermal unit having a reservoir of material at a temperature selected for applying thermal therapy to the selected body element of a patient,
a pocket attached to said therapy section sized to removably receive and retain said thermal unit,
long connecting means formed of an elastically deformable material and attached to said therapy section proximate one of said top and said bottom, said long connecting means having a left section extending outwardly from said left side a first length and a right section extending outwardly from said right side a second length,
long attaching means having a first attaching element attached to or formed with said left section of said long connecting means and a second attaching element attached to or formed with said right section of said long connecting means for removably attaching said left section and said right section together to form an opening adjustable in size to receive the selected body element of a patient therein and for attaching said therapy section to said selected body element to cause thermal energy from said thermal unit to be applied to said body element, said first attaching element and said second attaching element being formed to interact to secure themselves together,
short connecting means formed of an elastically deformable material attached to said therapy section proximate the other of said top and said bottom, said short connecting means having a left section extending outwardly from said left side a third length and a right section extending outwardly from said right side a fourth length, said third length and said fourth length together being less than said first length and said second length together, and
short attaching means having a first attaching element attached to or formed with said left section of said short connecting means and a second attaching element attached to or formed with said right section of said short connecting means for removably attaching said left section of said short connecting means and said right section of said short connecting means together to form an opening adjustable in size for positioning about the selected body element of a patient spaced from said long connecting means and for attaching said therapy section to said selected body element to cause thermal therapy from said thermal unit to be applied to said selected body element, said first attaching element and said second attaching element being formed to interact to secure themselves together;
positioning said thermal unit in said pocket;
stretching said therapy section about an element of the body selected to receive thermal therapy;
stretching said long connecting means about said element of the body to secure said therapy section snugly against said element of the body and to position said left section and said right section of said long connecting means proximate each other;
urging said first attaching element and said second attaching element of said long attaching means together to removably fasten said first attaching element to said second attaching element;
stretching said short connecting means about said element of the body to secure said therapy section snugly against said element of said body and to position said left section and said right section of said short connecting means proximate each other; and
urging said first attaching element and said second attaching element of said short attaching means together to removably fasten said first attaching element to said second attaching element.

19. The method of claim 18 further including
providing a strap formed of an elastically deformable material having a strap length, a strap first end, a strap second end and strap attaching means having a first strap attaching element proximate said strap first end and a second strap attaching element proximate said strap second end, said first element and said second element being configured to attach to each other;
stretching said strap about said wrap;
removably connecting said first element of said strap attaching means to one of said second element of said strap attaching means, said first element or said second element of said long attaching means and said first element or said second element of said short attaching means and removably connecting said second element of said strap attaching means to one of said first element of said strap attaching means, the other of said first element or said second element of said long attaching means and the other of said first element and said second element of said short attaching means.

20. The method of claim 19 wherein said selected body element is one of the ankle, the wrist, the elbow, the thigh, the calf, the upper arm, the shoulder, the torso, the neck, the lower arm and the knee.

21. A method of applying thermal therapy to a patient, said method comprising:
- providing a wrap having
  - a therapy section with a top, a bottom, a left side and a right side, said therapy section formed of an elastically deformable material and being sized for positioning in tension about one of the knee, ankle, thigh, calf, upper arm, lower arm, elbow, shoulder, neck and trunk of a patient,
  - a thermal unit having a reservoir of material at a temperature selected for applying thermal therapy to the shoulder of a patient,
  - a pocket attached to said therapy section sized to removably receive and retain said thermal unit,
  - long connecting means formed of an elastically deformable material and attached to said therapy section proximate one of said top and said bottom, said long connecting means having a left section extending outwardly from said left side a first length and a right section extending outwardly from said right side a second length,
  - long attaching means having a first attaching element attached to or formed with said left section of said long connecting means and a second attaching element attached to or formed with said right section of said long connecting means, said first attaching element and said second attaching element being formed to attach to each other and one of which being formed to attach to said elastically deformable material,
  - short connecting means formed of an elastically deformable material attached to said therapy section proximate the other of said top and said bottom, said short connecting means having a left section extending outwardly from said left side a third length and a right section extending outwardly from said right side a fourth length, said third length and said fourth length together being less than said first length and said second length together, and
  - short attaching means having a first attaching element attached to or formed with said left section of said short connecting means and a second attaching element attached to or formed with said right section of said short connecting means, said first attaching element and said second attaching element being formed to attach to each other and one of which is formed to attached to said elastically deformable material;
- providing a strap having a strap length, a strap first end, a strap second end and strap attaching means having a first element proximate said strap first end and a second element proximate said strap second end, said first element and said second element being configured to attach to each other and one of which being formed to attach to said elastically deformable material;
- positioning said thermal unit in said pocket;
- positioning said therapy section about one of the knee, ankle, thigh, calf, upper arm, lower arm, elbow, shoulder, neck and trunk of a patient and selectively securing said therapy section thereabout by one of
- stretching said long connecting means about one of the knee, ankle, thigh, calf, upper arm, lower arm, elbow and of a patient to snugly position said therapy section there against and to position said left section and said right section of said long connecting means proximate each other and then urging said first attaching element and said second attaching element of said long attaching means together to removably fasten said first attaching element to said second attaching element and then stretching said short connecting means about one of the knee, ankle, thigh, calf, upper arm, lower arm, elbow, shoulder and neck and trunk of a patient to secure said therapy section snugly against said element of said body and to position said left section and said right section of said short connecting means proximate each other and urging said first attaching element and said second attaching element of said short attaching means together to removably fasten said first attaching element to said second attaching element, positioning said left section of said long attaching means along one of the chest or back of a patient and positioning said right section along the other of one of the chest or back of a patient with said therapy section positioned about the shoulder of a patient and attaching said first attaching element of said long attaching means together with one of the first element and the second element of said strap, stretching said strap about the torso of the patient and urging the second attaching element of said long attaching means together with the other of said first attaching element and second element of said strap to snugly secure said therapy section to said shoulder,
- positioning said left section and said right section of said long attaching means about the torso of a patient wearing clothing that includes structure at the waist with said therapy section positioned against and about the torso and attaching said first attaching element of said long attaching means together with one of the first element and the second element of said strap, stretching said strap about the torso of the patient and urging the second attaching element of said long attaching means together with the other of said first attaching element and second element of said strap to snugly secure said therapy section to said torso and then positioning the therapy section and the short attaching means proximate the waist structure to be held there in place, and
- folding the therapy section to fit about the neck of a patient, positioning the therapy section about the neck of a patient and wrapping the strap about the therapy section and the neck and attaching the first element of said strap attaching means to one of said first elements and second elements of one of said long attaching means and said short attaching means and securing the second element of said strap attaching means to one of the other of said first elements and second elements of said long attaching means and short attaching means and to the therapy section itself.

22. A method of applying thermal therapy to a patient, said method comprising:
- providing a wrap having
  - a therapy section with a top, a bottom, a left side and a right side, said therapy section formed of a closed-cell neoprene with a first material laminated to one surface and a second material laminated to the opposite surface, said therapy section being sized for positioning in tension about one of the knee, ankle, thigh, calf, upper arm, lower arm, elbow, shoulder, neck and trunk of a patient, a thermal unit having a reservoir of material at a temperature selected for applying thermal therapy to the shoulder of a patient, a pocket attached to said therapy section sized to receive and retain said thermal unit, long connecting means formed of a closed-cell neoprene with a first material laminated to one surface and a second material laminated to the opposite surface and attached to said therapy section proximate one of said top and said bottom, said long connecting means having a left section extending outwardly from said left side a first length and a right section extending outwardly from said right side a second length, long attaching means having a hook portion of a hook and pile connecting system attached to or formed with said left section of said long connecting means and one of said first material and said second material of said right section being formed to be a pile section of said hook and pile connecting system attached to or formed with said right section of said long connecting means, short connecting means formed of a closed-cell neoprene with a first material laminated to one surface and a second material laminated to the opposite surface and attached to said therapy section proximate the other of said top and said bottom, said short connecting means having a left section extending outwardly from said left side a third length and a right section extending outwardly from said right side a fourth length, said third length and said fourth length together being less than said first length and said second length together, and short attaching means having a hook portion of a hook and pile connecting system attached to or formed with said left section of said short connecting means and one of said first material and said second material of said right section being formed to be a pile section of said hook and pile connecting system;

providing a strap having a strap length, a strap first end, a strap second end and strap attaching means having a hook portion of a hook and pile connecting system proximate said strap first end and one of said first material and said second material formed to be a pile portion of a hook and pile system formed or attached proximate said strap second end;

positioning said thermal unit in said pocket;

positioning said therapy section about one of the knee, ankle, thigh, calf, upper arm, lower arm, elbow, shoulder, neck and trunk of a patient and selectively securing said therapy section thereabout by one of stretching said long connecting means about one of the knee, ankle, thigh, calf, upper arm, lower arm, elbow, shoulder, neck and trunk of a patient to snugly position said therapy section there against and to position said hook portion and said pile portion of said long connecting means proximate each other and then urging them together to effect a removable connection and then stretching said short connecting means about one of the knee, ankle, thigh, calf, upper arm, lower arm, elbow, shoulder, neck and trunk of a patient to secure said therapy section snugly against said element of said body and to position said hook portion and said pile portion of said short connecting means proximate each other and urging them to effect a removable connection, positioning said left section of said long attaching means along one of the chest or back of a patient and positioning said right section along the other of one of the chest or back of a patient with said therapy section positioned about the shoulder of a patient and attaching said hook or pile portion of said long attaching means together with the corresponding hook or pile portion of said strap, stretching said strap about the torso of the patient and urging the other of said hook portion and said pile portion of said long attaching means together with the other of said corresponding hook portion and pile portion of said of said strap to snugly secure said therapy section to said shoulder, and positioning said left section and said right section of said long attaching means about the torso of a patient wearing clothing that includes structure at the waist with said therapy section positioned against and about the torso and attaching one of said hook portion and said pile portion of said long attaching means together with a corresponding hook and pile portion of said strap, stretching said strap about the torso of the patient and urging the second attaching element of said long attaching means together with the other of said hook portion and said pile portion of said strap to snugly secure said therapy section to said torso and then positioning the therapy section and the short attaching means proximate the waist structure to be held there in place.

23. The method of claim 22 wherein said first material and said second material are of the type to be a pile of a hook and pile type connector.

24. The method of claim 22 wherein said long connecting means is positioned about the portion of body of a patient proximate the knee, ankle, thigh, calf, upper arm, lower arm, elbow and trunk with the largest circumference in relation to the portion of the body about which the short connecting means is positioned.

25. The method of claim 22 wherein said first length and said second length are equal and wherein said third length and said fourth length are equal.

* * * * *